(12) United States Patent
McMichael

(10) Patent No.: US 6,575,169 B2
(45) Date of Patent: *Jun. 10, 2003

(54) METHOD AND APPARATUS FOR USE IN TREATING A PATIENT WITH ANY DRUG TO OPTIMIZE THERAPY AND PREVENT AN ADVERSE DRUG

(75) Inventor: John P. McMichael, Wexford, PA (US)

(73) Assignee: The RxFiles Corporation, Nokomis, FL (US)

( * ) Notice: Subject to any disclaimer, the term of this patent is extended or adjusted under 35 U.S.C. 154(b) by 93 days.

This patent is subject to a terminal disclaimer.

(21) Appl. No.: 09/832,090

(22) Filed: Apr. 10, 2001

(65) Prior Publication Data

US 2001/0020475 A1 Sep. 13, 2001

Related U.S. Application Data

(63) Continuation-in-part of application No. 09/816,906, filed on Mar. 23, 2001, and a continuation-in-part of application No. 09/644,503, filed on Aug. 24, 2000, and a continuation-in-part of application No. 09/348,592, filed on Jul. 6, 1999, now Pat. No. 6,276,116.

(51) Int. Cl.$^7$ .............................................. A61B 19/00
(52) U.S. Cl. ....................................... 128/898; 600/300
(58) Field of Search ................... 128/897–98; 600/300, 600/308, 347, 364–66, 368

(56) References Cited

U.S. PATENT DOCUMENTS

| | | | | |
|---|---|---|---|---|
| 5,365,948 A | 11/1994 | McMichael | ................. | 128/898 |
| 5,542,436 A | 8/1996 | McMichael | ................. | 128/897 |
| 5,694,950 A | 12/1997 | McMichael | ................. | 128/898 |
| 6,267,116 B1 * | 7/2001 | McMichael | ................. | 128/898 |

* cited by examiner

Primary Examiner—John P. Lacyk
(74) Attorney, Agent, or Firm—Gifford, Krass, Groh, Sprinkle, Anderson & Citkowski, P.C.

(57) ABSTRACT

A method and system for use in treating a patient receiving any drug to optimize therapy and to prevent an adverse drug response. This system employs surrogate markers or indicators, including blood levels of drug, to determine the next required dose for a patient. Virtually any indicator can be used as the surrogate marker. Surrogate markers could include any measure of the effectiveness of a drug's action. Given the effectiveness of the drug's action, relative to the surrogate markers, a change in drug dose is calculated by the system which uses a stochastic loop mechanism. Conversely, by employing this system, one could determine the expected result of a drug dose change based on the surrogate markers.

3 Claims, 2 Drawing Sheets

METHOD AND APPARATUS FOR USE IN TREATING A PATIENT WITH ANY DRUG TO OPTIMIZE THERAPY AND PREVENT AN ADVERSE DRUG

RELATED APPLICATIONS

The present patent application is a continuation-in-part of: U.S. patent application Ser. No. 09/348,592 filed on Jul. 6, 1999; now U.S. Pat. No. 6,276,116 U.S. patent application Ser. No. 09/644,503 filed on Aug. 24, 2000; and U.S. patent application Ser. No. 09/816,906 filed on Mar. 23, 2001, the entire contents of all three said applications are incorporated herein by reference thereto.

A portion of the disclosure of this patent document may contain material which is the subject of copyright protection. The copyright owner has no objection to the facsimile reproduction by anyone of the patent disclosure as it appears in the public patent files of the United States Patent and Trademark Office, but otherwise reserves all other rights in the copyrighted material.

FIELD OF THE INVENTION

The present invention relates to a method and system for use in treating a patient with any drug to optimize drug therapy and to prevent an adverse drug response. The present invention can utilize either drug levels or other surrogate markers to determine the effectiveness of the dosing regimen and, if necessary, to suggest a new more optimal drug dose.

BACKGROUND OF THE INVENTION

When a patient begins taking any medication for a length of time, a titration of the amount of drug taken by the patient is necessary in order to achieve the optimal benefit of the drug, and at the same time to prevent any undesirable side effects that taking too much of the drug could produce. Thus, there is a continuous balance between taking enough drug in order to gain the benefits from that drug and at the same time not taking so much drug as to illicit a toxic event.

There is large inter-individual variability in the patient pharmacokinetics of drugs. What may be an appropriate drug dose for one individual, may be too much or too little for another. Prior to this invention a physician was required to estimate the correct drug dosage for a patient and then to experiment with that dosage, usually by trial and error, until the correct dosage was achieved. Likewise, the FDA labeling of a drug suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate drug dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some drugs, but because the models are static and cannot adapt themselves to changes within a population or a patient, they are once again undesirable for dynamically determining drug dosages.

Expert systems have been developed using similar technology to predict drug dosages for immunosuppressant drugs (see, e.g., U.S. Pat. Nos. 5,365,948, 5,542,436 and 5,694,950). These algorithms, however, are not generic and only use immunosuppressant blood levels. Each algorithm is specific to an individual immunosuppressant drug. As it stands, these inventions cannot be applied to other drugs and do not have a non-linear feedback loop mechanism.

SUMMARY OF THE INVENTION

The term "drug" as used herein includes, but is not limited to, substances which are conventionally called drugs, vaccines, serums, vitamin antagonists, medications, biological substances, and all substances derived from and/or related to the foregoing substances.

The present invention provides a method for calculating a new dose of a drug for a patient using said drug, comprising the steps of: accepting as a first input the patient's current drug dose; accepting as a second input the maximum dose of the drug; accepting as a third input one or more numerical markers indicating a response of the patient; calculating said new dose, wherein said new dose is a function of said current dose minus the ratio of the change in numerical markers and the ratio of said current dose to said maximum dose plus the percent of individual patient response multiplied by a response factor; and said calculating step includes calculating said new dose based on the equation $$NDD=CDD-\{[((CDNM-DDNM)/CDNM)/(1+(CDD/HIGH))]\times CDD\}+LV$$

and:

$$EDNM=[((CDD-PDD)/PDD)\times(1+(PDD/HIGH))\times PDNM]+PDNM$$

and:
if CDNM<DDNM, and EDNM>CDNM,
or if CDNM>DDNM, and EDNM<CDNM,
then $$LV=(RESPONSE\times CDD)\times[(EDNM-CDNM)/CDNM]/[1.3^{\wedge}(CDD/HIGH)],$$

but if CDNM<DDNM, and EDNM<CDNM,
or if CDNM>DDNM, and EDNM>CDNM,
then $$LV=-1\times(RESPONSE\times CDD)\times[(CDNM-EDNM)/CDNM]/[1.3^{\wedge}(CDD/HIGH)],$$

wherein:
NDD=New Drug Dose
CDD=Current Drug Dose
CDNM=Current Drug Numerical Marker
DDNM=Desired Drug Numerical Marker
HIGH=The input parameter that is the high dose range for a particular drug
EDNM=Expected Drug Numerical Marker
PDD=Previous Drug Dose
PDNM=Previous Drug Numerical Marker
RESPONSE=Percent of total dose available for individualizing patient dose
1.3^(CDD/HIGH)=1.3 raised to an exponent of (CDD/HIGH).

According to the present invention, patient dosing occurs through a cyclic series of events, depicted in flow chart form in FIG. 1. After an initial examination, an initial dose of a drug (therapeutic agent) is prescribed and administered by a physician for a patient. The initial dose is based on the FDA recommended dosage found on the drug label. The drug dose is further refined upon repeated dosing by the physician based on the patient's response to the drug. Too much drug could cause the patient to experience toxic drug effects, and the drug dose would need to be reduced. Too little drug could cause the patient not to receive the benefit the drug therapy could offer, and the dosage would need to be increased.

This invention has at least two preferred embodiments; one which uses actual numerical surrogate markers to calculate a dose, and another embodiment that uses percentages as the numerical input for the surrogate markers.

DETAILED DESCRIPTION OF THE INVENTION

Figure 1:
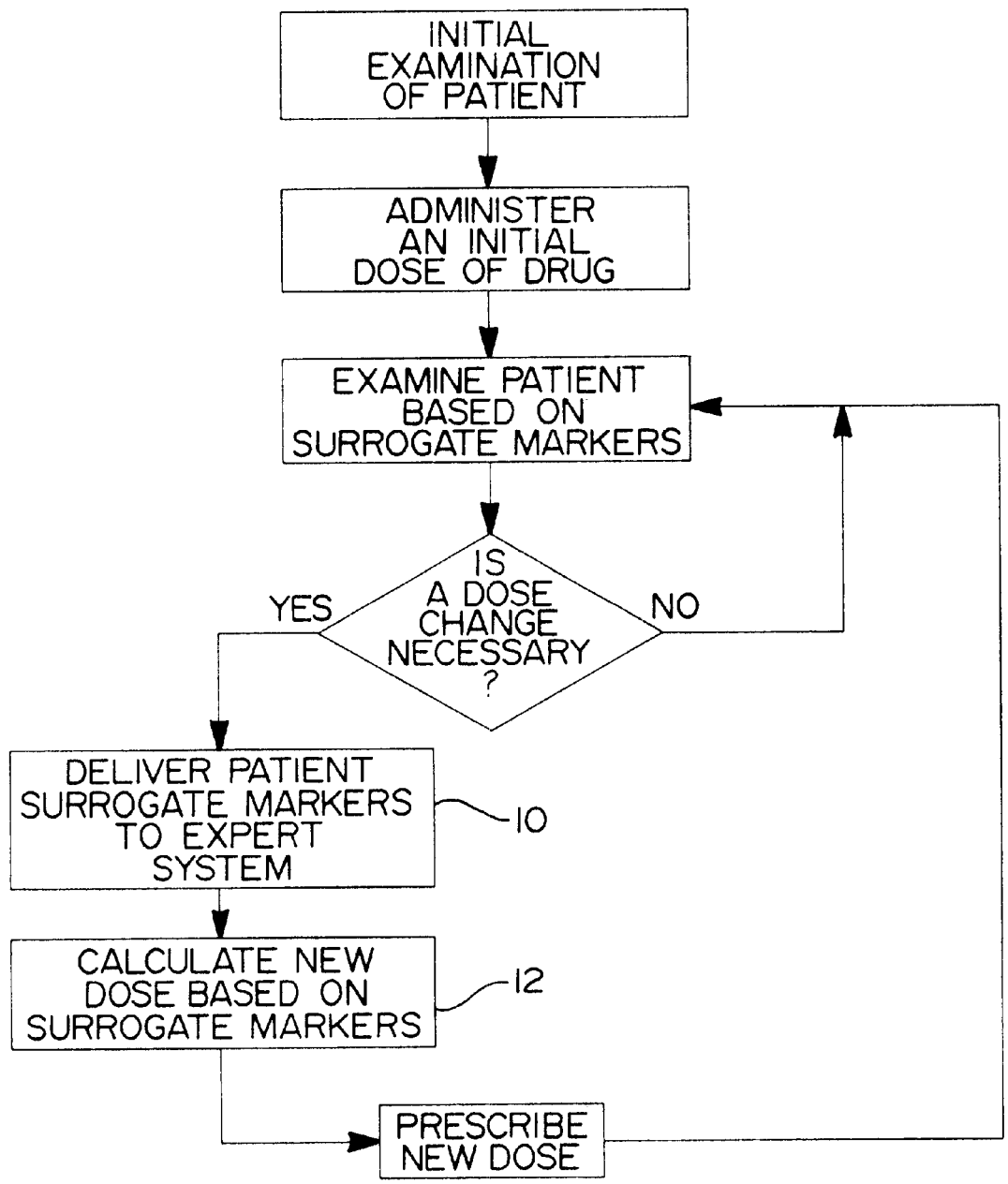
FIG. 1 shows a flow chart of the process by which new doses of a drug are determined, according to the method of the invention described herein.

A method of this invention for use in treating a patient receiving any drug to optimize therapy and to prevent an adverse drug response can be implemented in two different embodiments, two of which will each be described separately. FIG. 1 shows a flow chart of the overall process of treating a patient using this expert system. The actual expert system, however, performs only the steps shown in blocks 10 and 12 of the flow chart.

Figure 2:
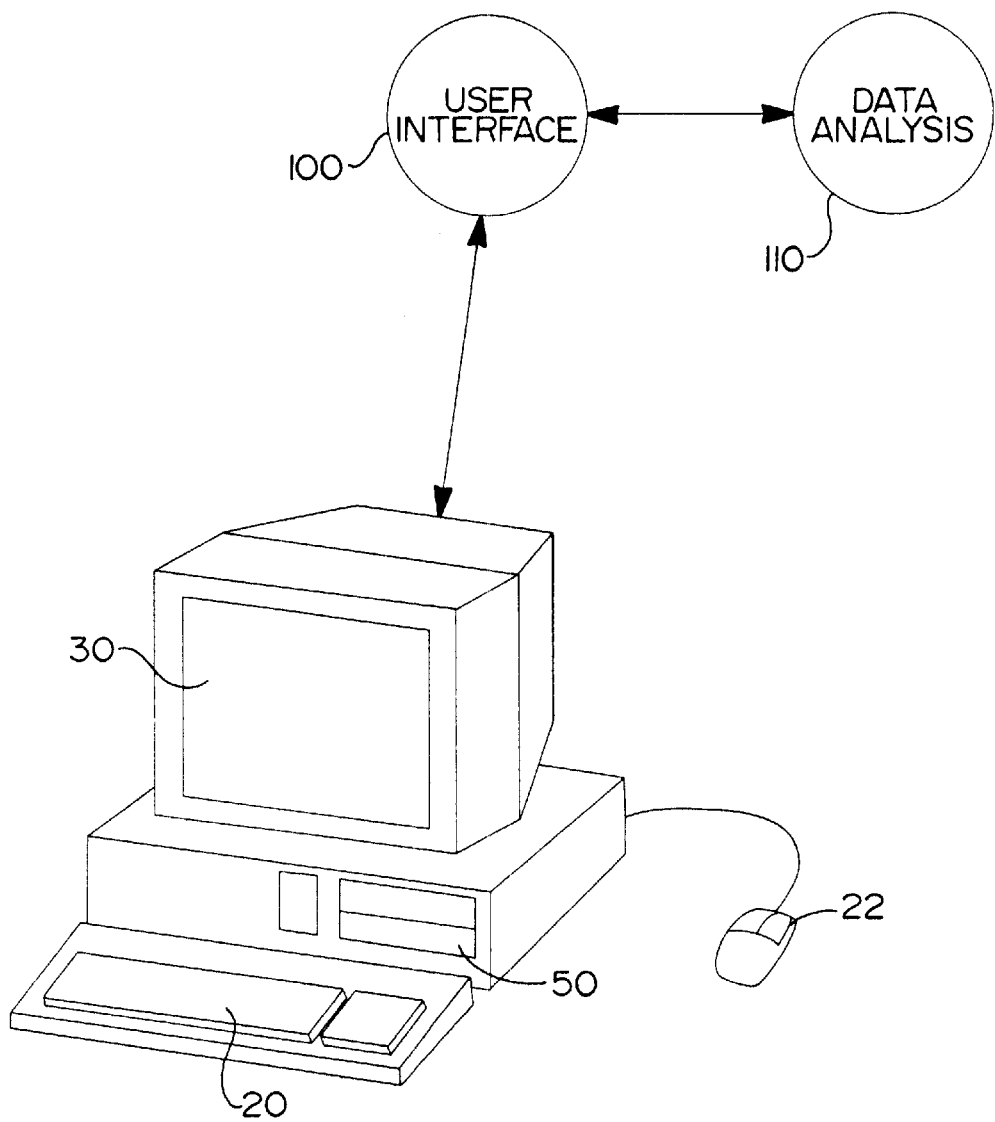
FIG. 2 shows an apparatus for use in calculating new doses of a drug according to the present invention.

This expert system includes a general purpose computer, shown in FIG. 2, comprising an input means, preferably a keyboard 20 and/or a mouse 22, an output means 30, preferably a video display screen, a data storage means 50, preferably a hard disk drive, and a processor. The expert computer program receives input data from a physician regarding the patient's current drug dose, the maximal dose range for the drug, and the percent response of the patient based on the surrogate markers used to monitor the drug. Also characterized is the patient's response to the last dosing cycle as well as a dose response constant. This allows the expert system to individualize the patient dosing based on the patient's individual response to the drug. The system calculates a new dosage based on the data input by the physician. The software portion of the invention includes a user interface portion 100 to receive the input data and to output the new dosage information, and a data analysis portion 110, which calculates the new dosage information based on the input data.

The present invention thus provides an apparatus for calculating a new dose of a drug for a patient, comprising: first means for accepting as input one or more markers which indicate said patient's response to a dose of a drug; second means for accepting as input the patient's current drug dose; third means for accepting as input the maximum dose of the drug; fourth means for calculating said new dose of the drug as a function of said markers, said current drug dose, and said maximum drug dose; and said new dose is calculated by the following equation:

$$NDD=CDD-\{[((CDNM-DDNM)/CDNM)/(1+(CDD/HIGH))]\times CDD\}+LV$$

and:

$$EDNM=[((CDD-PDD)/PDD)\times(1+(PDD/HIGH))\times PDNM]+PDNM$$

and:
if CDNM<DDNM, and EDNM>CDNM,
or if CDNM>DDNM, and EDNM<CDNM,
then $$LV=(RESPONSE\times CDD)\times[(EDNM-CDNM)/CDNM]/[1.3^{\wedge}(CDD/HIGH)],$$

but if CDNM<DDNM, and EDNM<CDNM,
or if CDNM>DDNM, and EDNM>CDNM,
then $$LV=-1\times(RESPONSE\times CDD)\times[(CDNM-EDNM)/CDNM]/[1.3^{\wedge}(CDD/HIGH)],$$

wherein:
NDD=New Drug Dose
CDD=Current Drug Dose
CDNM=Current Drug Numerical Marker
DDNM=Desired Drug Numerical Marker
HIGH=The input parameter that is the high dose range for a particular drug
EDNM=Expected Drug Numerical Marker
PDD=Previous Drug Dose
PDNM=Previous Drug Numerical Marker
RESPONSE=Percent of total dose available for individualizing patient dose
$1.3^{\wedge}(CDD/HIGH)=1.3$ raised to an exponent of (CDD/HIGH).

Numerical Surrogate Markers Embodiment

A physician prescribes a drug for a patient based on the FDA recommended dose on the label of the drug. The physician then re-evaluates the patient, usually daily, either in person or remotely depending on the agent being prescribed. During the subsequent evaluations by the physician, the surrogate markers are monitored and sequentially compared to determine if there are any toxicities associated with the drug. Also the numerical markers will evaluated to see if the desired effect of the drug is being achieved. Based on this evaluation by the physician, the current drug dose, the current drug numerical marker, the desired drug numerical marker, and the previous drug numerical marker are then input into the embodiment and the new drug dose is calculated based on the equation:

$$NDD=CDD-\{[((CDNM-DDNM)/CDNM)/(1+(CDD/HIGH))]\times CDD\}+LV$$

and:

$$EDNM=[((CDD-PDD)/PDD)\times(1+(PDD/HIGH))\times PDNM]+PDNM$$

and:
if CDNM<DDNM, and EDNM>CDNM,
or if CDNM>DDNM, and EDNM<CDNM,
then $$LV=(RESPONSE\times CDD)\times[(EDNM-CDNM)/CDNM]/[1.3^{\wedge}(CDD/HIGH)],$$

but if CDNM<DDNM, and EDNM<CDNM,
or if CDNM>DDNM, and EDNM>CDNM,
then $$LV=-1\times(RESPONSE\times CDD)\times[(CDNM-EDNM)/CDNM]/[1.3^{\wedge}(CDD/HIGH)],$$

wherein:
NDD=New Drug Dose
CDD=Current Drug Dose
CDNM=Current Drug Numerical Marker
DDNM=Desired Drug Numerical Marker HIGH=The input parameter that is the high dose range for a particular drug
EDNM=Expected Drug Numerical Marker
PDD=Previous Drug Dose
PDNM=Previous Drug Numerical Marker
RESPONSE=Percent of total dose available for individualizing patient dose
$1.3\textasciicircum(CDD/HIGH)$=1.3 raised to an exponent of (CDD/HIGH).

Percentage Surrogate Markers Embodiment

In this preferred embodiment, a physician prescribes a drug for a patient based on the FDA recommended dose on the label of the drug. The physician then re-evaluates the patient, usually daily, either in person or remotely depending on the agent being prescribed. During the subsequent evaluations by the physician, the surrogate markers are monitored and sequentially compared to determine if there are any toxicities associated with the drug. Also the surrogate markers are evaluated to see if the desired effect of the drug is being achieved. Based on this evaluation by the physician, the current drug dose, and the percent response of the patient to the last dosing based on a surrogate marker are then input into the system and the new drug dose is calculated based on the equation:

$$NDD=CDD-\{[((PDR-100)/PDR)/1+(CDD/HIGH))]\times CDD\}+LV$$

where:

$$LV=\{(RESPONSE\times CDD)\times[(100-RES)\times 0.01]\}/[1.3\textasciicircum(CDD/HIGH)]$$

and wherein:
NDD=New Drug Dose
CDD=Current Drug Dose
PDR=Percent response of patient to surrogate marker
RES=Percent response of patient to last dosing based on surrogate marker
HIGH=The input parameter that is the high dose range for a particular drug
RESPONSE=Percent of total dose available for individualizing patient dose
$1.3\textasciicircum(CDD/HIGH)$=1.3 raised to an exponent of (CDD/HIGH).

This cycle of repeated re-evaluation of the numerical surrogate markers is continued as long as the patient is required to take the drug.

Two embodiments of the invention have been described, one using numerical markers, and one using a percentage surrogate marker. Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method for calculating a new dose of a drug for a patient using said drug, comprising the steps of:
   accepting as a first input the patient's current drug dose;
   accepting as a second input the maximum dose of the drug;
   accepting as a third input one or more numerical markers indicating a response of the patient;
   calculating said new dose, wherein said new dose is a function of said current dose minus the ratio of the change in numerical markers and the ratio of said current dose to said maximum dose plus the percent of individual patient response multiplied by a response factor; and said calculating step includes calculating said new dose based on the equation $$NDD=CDD-\{[((CDNM-DDNM)/CDNM)/(1+(CDD/HIGH))]\times CDD\}+LV$$

and:

$$EDNM=[((CDD-PDD)/PDD)\times(1+(PDD/HIGH))\times PDNM]+PDNM$$

and:
if CDNM<DDNM, and EDNM>CDNM,
or if CDNM>DDNM, and EDNM<CDNM,
then $$LV=(RESPONSE\times CDD)\times[(EDNM-CDNM)/CDNM]/[1.3\textasciicircum(CDD/HIGH)],$$

but if CDNM<DDNM, and EDNM<CDNM,
or if CDNM>DDNM, and EDNM>CDNM,
then $$LV=-1\times(RESPONSE\times CDD)\times[(CDNM-EDNM)/CDNM]/[1.3\textasciicircum(CDD/HIGH)],$$

wherein:
NDD=New Drug Dose
CDD=Current Drug Dose
CDNM=Current Drug Numerical Marker
DDNM=Desired Drug Numerical Marker
HIGH=The input parameter that is the high dose range for a particular drug
EDNM=Expected Drug Numerical Marker
PDD=Previous Drug Dose
PDNM=Previous Drug Numerical Marker
RESPONSE=Percent of total dose available for individualizing patient dose
$1.3\textasciicircum(CDD/HIGH)$=1.3 raised to an exponent of (CDD/HIGH).

2. An apparatus for calculating a new dose of a drug for a patient, comprising:
   first means for accepting as input one or more markers which indicate said patient's response to a dose of a drug;
   second means for accepting as input the patient's current drug dose;
   third means for accepting as input the maximum dose of the drug;
   fourth means for calculating said new dose of the drug as a function of said markers, said current drug dose, and said maximum drug dose; and
   said new dose is calculated by the following equation:

$$NDD=CDD-\{[((CDNM-DDNM)/CDNM)/(1+(CDD/HIGH))]\times CDD\}+LV$$

and:

$$EDNM=[((CDD-PDD)/PDD)\times(1+(PDD/HIGH))\times PDNM]+PDNM$$

and:
if CDNM<DDNM, and EDNM>CDNM,
or if CDNM>DDNM, and EDNM<CDNM,
then $$LV=(RESPONSE-CDD)\times[(EDNM-CDNM)/CDNM[1.3\textasciicircum(CDD/HIGH)],$$

but if CDNM<DDNM, and EDNM<CDNM,
or if CDNM>DDNM, and EDNM>CDNM,
then $$LV = -1 \times (RESPONSE \times CDD) \times [(CDNM-EDNM)/CDNM]/[1.3^{\wedge}(CDD/HIGH)],$$

wherein:

NDD=New Drug Dose
CDD=Current Drug Dose
CDNM=Current Drug Numerical Marker
DDNM=Desired Drug Numerical Marker
HIGH=The input parameter that is the high dose range for a particular drug
EDNM=Expected Drug Numerical Marker
PDD=Previous Drug Dose
PDNM=Previous Drug Numerical Marker
RESPONSE=Percent of total dose available for individualizing patient dose
1.3^(CDD/HIGH)=1.3 raised to an exponent of (CDD/HIGH).

3. The apparatus of claim 2, wherein:
said markers are actual numerical markers.

* * * * *

UNITED STATES PATENT AND TRADEMARK OFFICE
CERTIFICATE OF CORRECTION

PATENT NO.    : 6,575,169 B2
DATED         : June 10, 2003
INVENTOR(S)   : John P. McMichael It is certified that error appears in the above-identified patent and that said Letters Patent is hereby corrected as shown below:

<u>Title page, Item [54] and Column 1, line 4,</u>
Title, after "ADVERSE DRUG" insert -- RESPONCE --.

<u>Column 5,</u>
Line 26, replace "/PDR)/1+" with -- /PDR)/(1+ --.

<u>Column 6,</u>
Line 66, replace "LV=(RESPONSE-CDD)×[(EDNM-CDNM)/CDNM][1.3^(CDD/"
with -- LV=(RESPONSE×CDD)×[(EDNM-CDNM)/(CDNM]/[1.3^(CDI --

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,575,169 B2
DATED : June 10, 2003
INVENTOR(S) : John P. McMichael

It is certified that error appears in the above-identified patent and that said Letters Patent is hereby corrected as shown below:

Title page, Item [54] and Column 1, line 4,
Title, after "ADVERSE DRUG" insert -- RESPONSE --.

Column 5,
Line 26, replace "/PDR)/1+" with -- /PDR)/(1+ --.

Column 6,
Line 66, replace "LV=(RESPONSE-CDD)×[(EDNM-CDNM)/CDNM][1.3^(CDD/"
with -- LV=(RESPONSE×CDD)×[(EDNM-CDNM)/(CDNM]/[1.3^(CDI --.

This certificate supersedes Certificate of Correction issued June 8, 2004.

Signed and Sealed this

Eleventh Day of October, 2005

JON W. DUDAS
*Director of the United States Patent and Trademark Office*